(12) United States Patent
Lee et al.

(10) Patent No.: US 10,363,395 B2
(45) Date of Patent: Jul. 30, 2019

(54) DIRECTION-CONTROLLABLE CATHETER USING DRUG INJECTION CHANNEL

(71) Applicant: Korea Advanced Institute of Science And Technology, Daejeon (KR)

(72) Inventors: Doo Yong Lee, Daejeon (KR); Hye Hyun Han, Daejeon (KR); Yun Jin Gu, Daejeon (KR); Seung Gyu Kang, Daejeon (KR); Myeong Jin Kim, Daejeon (KR); Cheong Jun Kim, Daejeon (KR); Seong Pil Byeon, Daejeon (KR); Young Gi Jung, Daejeon (KR); Su Bon Kim, Daejeon (KR); Hyun Seok Lee, Daejeon (KR); Dong Myoung Lee, Daejeon (KR); Su Hwan Park, Daejeon (KR); Ji Hye Hwang, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/563,175

(22) PCT Filed: Apr. 1, 2015

(86) PCT No.: PCT/KR2015/003232
§ 371 (c)(1),
(2) Date: Sep. 29, 2017

(87) PCT Pub. No.: WO2016/159411
PCT Pub. Date: Oct. 6, 2016

(65) Prior Publication Data
US 2018/0085556 A1    Mar. 29, 2018

(30) Foreign Application Priority Data

Mar. 31, 2015    (KR) .................... 10-2015-0045299

(51) Int. Cl.
*A61M 31/00* (2006.01)
*A61M 37/00* (2006.01)
(Continued)

(52) U.S. Cl.
CPC .... *A61M 25/0084* (2013.01); *A61M 25/0054* (2013.01); *A61M 25/0075* (2013.01);
(Continued)

(58) Field of Classification Search
CPC .......... A61M 25/0074; A61M 25/0105; A61M 2025/0018; A61M 25/00; A61M 25/0054; A61M 25/0075; A61M 25/0138
See application file for complete search history.

(56) References Cited

U.S. PATENT DOCUMENTS 5,476,100 A * 12/1995 Galel ................ A61M 25/0155
                                                       600/466
6,024,730 A *  2/2000 Pagan ............... A61M 25/0054
                                                       604/264
(Continued)

*Primary Examiner* — Rebecca E Eisenberg
(74) *Attorney, Agent, or Firm* — Foley & Lardner LLP

(57) ABSTRACT

The present invention relates to a direction-controllable drug injection catheter. According to the present invention, provided is the catheter extending along a central axis "A" including a drug injection part in which a drug injection channel has been formed; a channel opening and closing means which opens and closes the drug injection channel; and a steering structure which is rotationally asymmetric with respect to the central axis "A" and varies according to a pressure change of the drug injection channel for the purpose of steering.

10 Claims, 9 Drawing Sheets

(51) Int. Cl.
  *A61M 25/00* (2006.01)
  *A61M 25/01* (2006.01)
  *A61M 25/06* (2006.01)
  *A61M 25/09* (2006.01)

(52) U.S. Cl.
  CPC .... *A61M 25/0105* (2013.01); *A61M 25/0138* (2013.01); *A61M 25/0155* (2013.01); *A61M 25/0612* (2013.01); *A61M 25/0074* (2013.01); *A61M 25/0905* (2013.01); *A61M 2025/0018* (2013.01)

(56) References Cited

U.S. PATENT DOCUMENTS

| | | | |
|---|---|---|---|
| 6,506,196 B1* | 1/2003 | Laufer | A61B 17/0057 227/175.1 |
| 6,746,422 B1* | 6/2004 | Noriega | A61M 25/0138 604/95.05 |
| 2003/0139793 A1* | 7/2003 | Hill | A61M 25/0138 607/116 |
| 2004/0059257 A1* | 3/2004 | Gaber | A61M 25/0138 600/585 |
| 2004/0220470 A1* | 11/2004 | Karmarkar | G01R 33/287 600/423 |
| 2007/0060997 A1* | 3/2007 | de Boer | A61F 2/958 623/1.11 |
| 2007/0100235 A1* | 5/2007 | Kennedy, II | A61B 6/504 600/434 |
| 2007/0213671 A1* | 9/2007 | Hiatt | A61M 25/007 604/164.01 |
| 2015/0088090 A1* | 3/2015 | Macy, Jr. | A61M 25/007 604/500 |
| 2017/0215694 A1* | 8/2017 | Truckai | A61B 1/018 |

* cited by examiner

-Prior Art-

DIRECTION-CONTROLLABLE CATHETER USING DRUG INJECTION CHANNEL

TECHNICAL FIELD

The present disclosure relates to a catheter and more particularly to a direction-controllable catheter.

BACKGROUND ART

A catheter is a thin and long tube-shaped medical treatment tool. The catheter is inserted into human body and is used to diagnose and cure a disease such as drug injection to a lesion or removal of tumor.

In vascular intervention, after the catheter enters the blood vessel where a lesion exists, the lesion is treated by injecting drugs. If the drug is delivered to a tissue outside the lesion, the tissue outside the lesion necrotizes. Therefore, it is important to position the front end of the catheter as close to the lesion as possible. Accordingly, in a blood vessel with many branches, the catheter capable of steering the front end of the catheter in a desired direction is being developed and used. FIG. 1 is a cross sectional view of a conventional direction-controllable drug injection catheter. Referring to FIG. 1, the catheter 10 includes a flexible tube 11, a drug injection channel 12c formed within the flexible tube 11, two wire channels 12a and 12b formed to have the drug injection channel 12c placed therebetween, and two steering wires 13a and 13b which are positioned in the two wire channels 12a and 12b respectively. The catheter 10 is steered by the two steering wires 13a and 13b. However, in addition to the conventional direction-controllable drug injection channel, two steering channels through which the two steering wires pass respectively are included, so that there is a limit to reduce the thickness of the catheter. Also, the conventional direction-controllable drug injection catheter has a complex structure because it includes a separate configuration for steering.

DISCLOSURE

Technical Problem

The object of the present invention is to significantly reduce the thickness of a direction-controllable drug injection catheter and to simplify the structure of the catheter.

Technical Solution

To achieve the object of the present invention, according to one embodiment of the present invention, provided is a catheter extending along a central axis "A" including a drug injection part in which a drug injection channel has been formed; a channel opening and closing means which opens and closes the drug injection channel; and a steering structure which is rotationally asymmetric with respect to the central axis "A" and varies according to a pressure change of the drug injection channel for the purpose of steering.

The steering structure may include a support which is bonded to one side outer surface of the drug injection part.

The support may include a base part, and a plurality of bonding portions which protrude from the base part and have ends bonded to the drug injection part.

The plurality of the bonding portions may be disposed in a row along the extension direction of the drug injection channel, and wherein a gap may be formed between two adjacent bonding portions among the plurality of the bonding portions.

The bonding portion may have a shape which becomes narrower toward the end thereof.

In the base part, a plurality of incision portions may be formed on the opposite side to the bonding portion, and the incision portion may be located corresponding to the gap.

The support may be made of a material having a modulus of elasticity greater than that of the drug injection part.

The channel opening and closing means may include a film-shaped fracture portion which is installed on the drug injection channel and is destroyed by a pressure of the drug.

The channel opening and closing means may include a support wall which is installed on the drug injection channel and has a through-hole formed therein, and an opening and closing member which opens and closes the through-hole. The opening and closing member may include a cover which is located further downstream than the support wall and opens and closes the through-hole, an elastic support which is located further upstream than the support wall, and an extension rod which passes through the through-hole and connects the cover with the elastic support. The elastic support may include a plurality of support wings which radially extend outwardly from the extension rod and of which ends contact the support wall.

The drug injection channel may be eccentrically located with respect to the whole central axis of the catheter. The support may be located on the opposite side to the eccentric direction of the drug injection channel.

Advantageous Effects

All of the above-described objects of the present invention can be achieved. Specifically, the catheter according to the embodiment of the present invention includes a drug injection part in which a drug injection channel has been formed; a support which includes a base part, and a plurality of bonding portions which protrude from the base part and have ends bonded to one side outer surface of the drug injection part; and a channel opening and closing means which opens and closes the drug injection channel. The plurality of the bonding portions are disposed in a row along the extension direction of the drug injection channel, and a gap is formed between two adjacent bonding portions among the plurality of the bonding portions. Therefore, the steering is possible only by controlling the pressure within the drug injection channel, so that the thickness of the catheter can be significantly reduced compared to that of the conventional catheter and the structure of the catheter becomes simpler.

MODE FOR INVENTION

Hereafter, the configuration and operation of an embodiment of the present invention will be described in detail with reference to the drawings.

Figure 1:
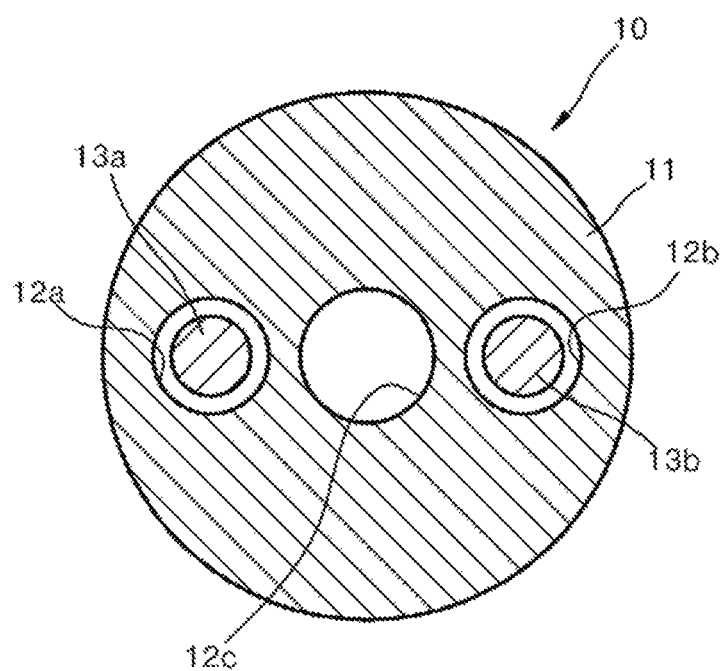
FIG. 1 is a cross sectional view showing a conventional direction-controllable drug injection catheter.
Figure 2:
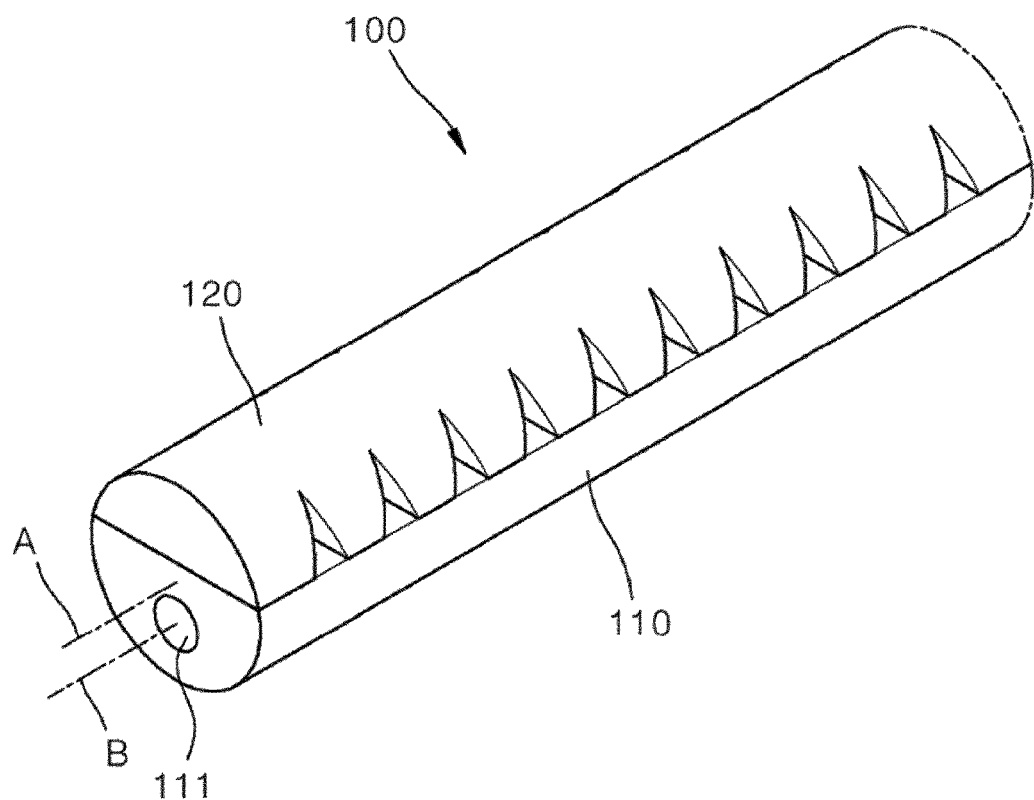
FIG. 2 is a perspective view which shows a front end of a direction-controllable drug injection catheter according to an embodiment of the present invention and shows that the front end has extended in a straight line.
Figure 3:
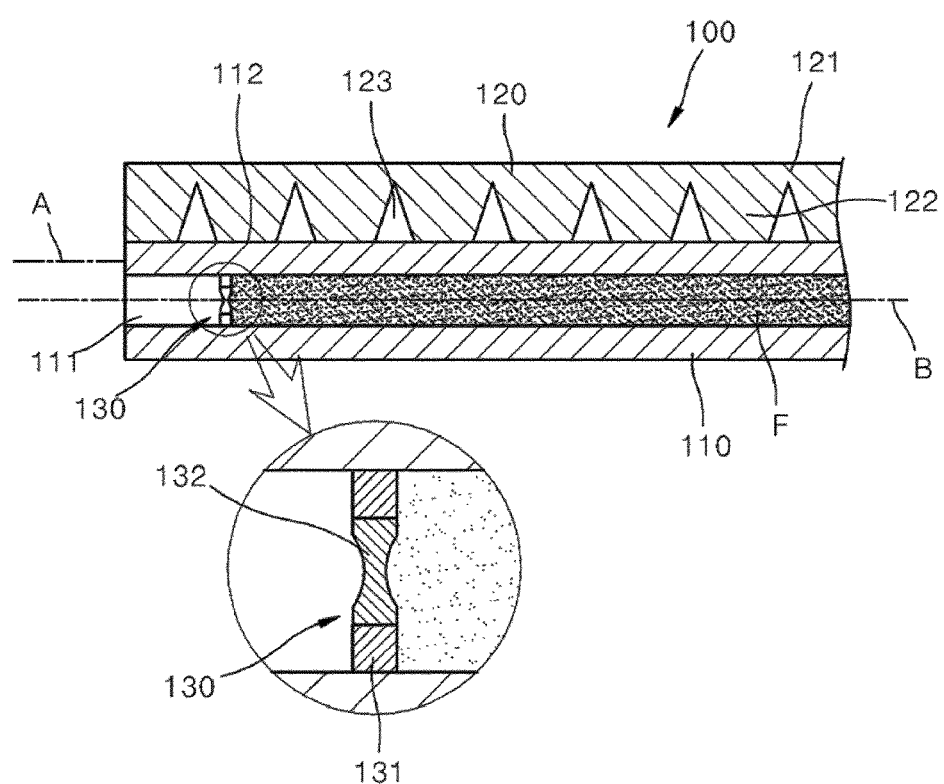
FIG. 3 is a longitudinal sectional view of the catheter shown in FIG. 2.

FIGS. 2 and 3 are a perspective view and a longitudinal sectional view of a front end of a direction-controllable drug injection catheter according to an embodiment of the present invention, which show that the front end has extended in a straight line. Referring to FIGS. 2 and 3, a catheter 100 according to the embodiment of the present invention has generally a circular cross section and extends along a central axis "A". The catheter 100 includes a drug injection part 110, a support 120, and a channel opening and closing means 130.

The drug injection part 110 extends along the central axis "A" and is made of a flexible material which is easily bent. A drug injection channel 111 through which a drug "F" passes is formed within the drug injection part 110. The drug injection channel 111 extends in parallel with the central axis "A" and is eccentrically located with respect to the central axis "A". That is, the central axis "A" of the catheter 100 and a central axis "B" of the drug injection channel 111 are parallel with each other and spaced apart from each other. The drug injection channel 111 is opened and closed by the channel opening and closing means 130. A flat bonding surface 112 to which the support 120 is bonded is formed on one side of the drug injection part 110.

The support 120 is bonded to the one side of the drug injection part 110 and extends along the central axis "A". The support 120 is an example of a steering structure which is rotationally asymmetric with respect to the central axis "A" disclosed in the patent claims. The steering structure is located only on one side of the drug injection channel and is changed according to the pressure change of the drug injection channel for steering. The support 120 is made of a flexible material in such a manner as to be bent together with the drug injection part 110. The support 120 is made of a material having a modulus of elasticity greater than that of the drug injection part 110 because the support 120 functions to structurally support the drug injection part 110. Preferably, the drug injection part 110 is made of rubber, and the support 120 is made of an elastic polymer material. On the opposite side to the drug injection channel 111 eccentrically located with respect to the central axis "A" of the catheter, the support 120 is bonded to the bonding surface 112 formed on the drug injection part 110. The support 120 includes a base part 121 and a plurality of bonding portions 122 protruding from the base part 121. The base part 121 is continuously formed along the longitudinal direction of the drug injection channel 111. The plurality of the bonding portions 122 protrude from the base part 121 and are arranged in a row along the longitudinal direction of the drug injection channel 111. The end of the bonding portion 122 is bonded to the bonding surface 112 formed on one side of the drug injection part 110. The bonding portion 122 becomes narrower toward the end thereof such that a gap is formed between two adjacent bonding portions 122. The two adjacent bonding portions 122 are connected to each other at the base part 121. A plurality of the gaps 123 are formed along the longitudinal direction of the drug injection channel 111. Due to the plurality of gaps 123, the catheter 100 can be easily bent in a direction in which a distance between the ends of the two bonding portions 122 is reduced.

The channel opening and closing means 130 is installed in the drug injection part 110 and opens and closes the drug injection channel 111. The channel opening and closing means 130 includes a support wall 131 and a fracture portion 132. The support wall 131 is fixed on the wall of the drug injection channel 111. The fracture portion 132 is coupled to the central portion of the support wall 131. The fracture portion 132 is in the form of a film. When a pressure of the drug "F" becomes higher than a certain value in the drug injection channel 111, the fracture portion 132 is destroyed and opens the drug injection channel 111.

Figure 4:
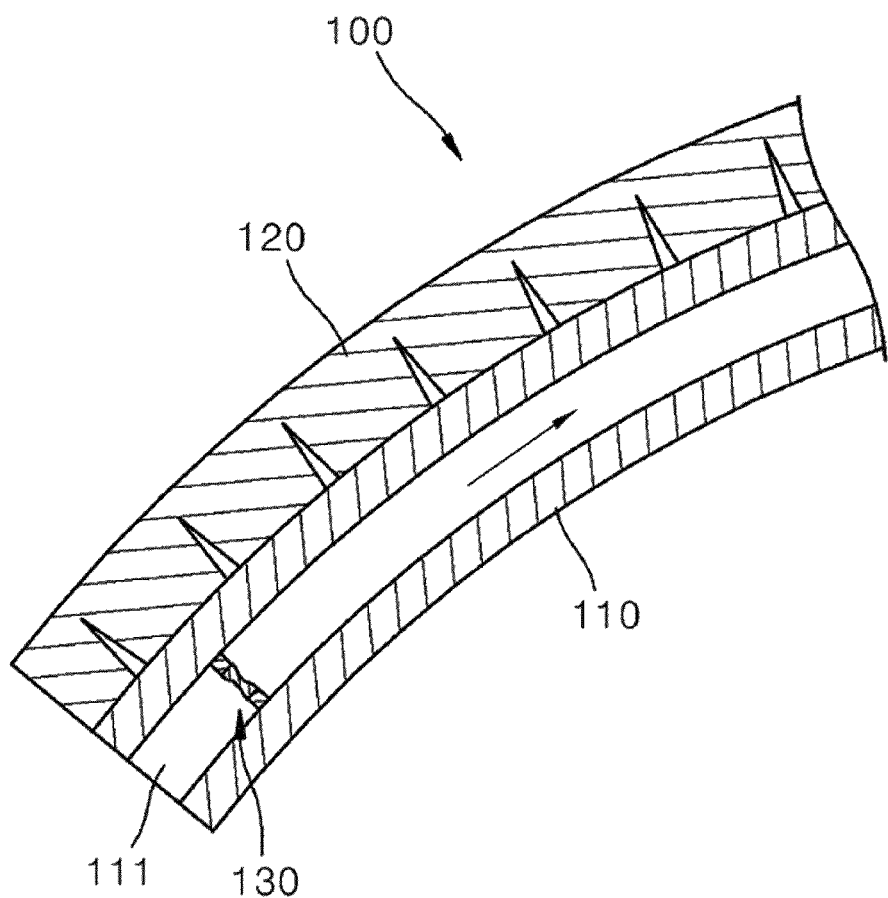
FIG. 4 is a longitudinal sectional view of the catheter shown in FIG. 2, which shows that the front end has been bent for direction control.
Figure 5:
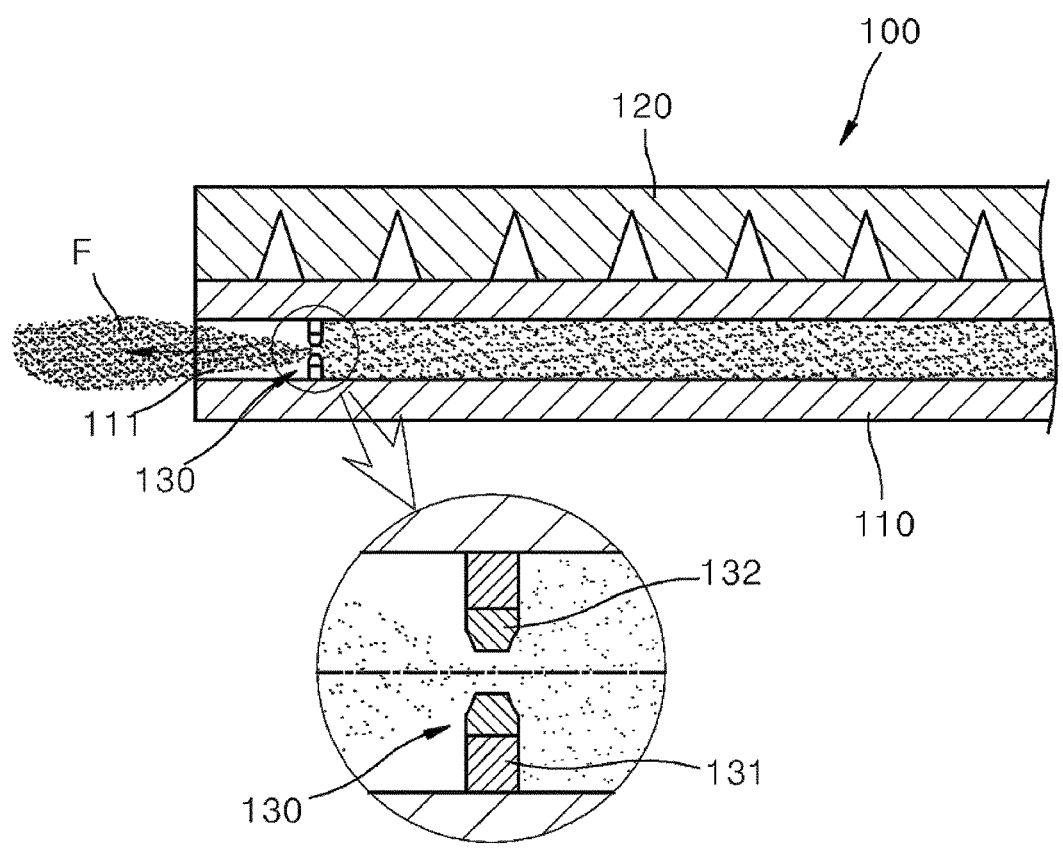
FIG. 5 is a longitudinal sectional view of the catheter shown in FIG. 2, which shows that drug is released.

While the catheter 100 has been described above focusing on its configuration, the following description will focus on the operation of the catheter 100 in detail. Referring to FIG. 3, the drug "F" is filled in the drug injection channel 111. Without releasing the drug "F" filled in the drug injection channel 111 to the outside through the channel opening and closing means 130, the front end of the catheter 100 extends, as shown, in a straight line. In the state shown in FIG. 3, the catheter 100 is inserted. When the catheter 100 encounters a branch point while being inserted in the state of FIG. 3, the drug "F" in the drug injection channel 111 is inhaled in an opposite direction to the direction in which the catheter is inserted, so that a negative pressure is formed in the catheter 100. As a result, as shown in FIG. 4, the front end of the catheter 100 is bent and thus steering becomes possible. The direction of entry of the catheter 100 can be changed into a desired direction by rotating the catheter 100. Also, a degree to which the catheter 100 is bent (radius of curvature) can be controlled according to the magnitude of the negative pressure formed in the drug injection channel 111. By using the state shown in FIGS. 3 and 4, the front end of the catheter 100 is able to approach as close to a desired position as possible. Then, the pressure within the drug injection channel 111 is increased over a certain value by injecting the drug "F", and thus, the fracture portion 132 of the channel opening and closing means 130 is fractured. Accordingly, as shown in FIG. 5, the drug "F" is released to the outside.

Figure 6:
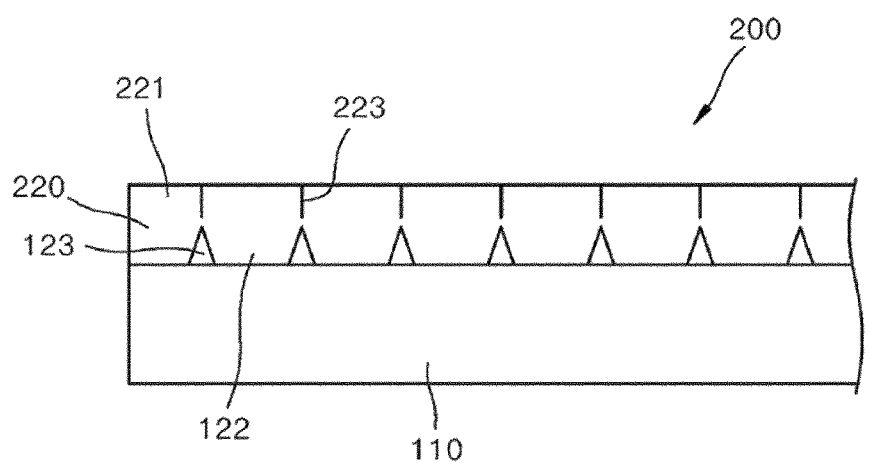
FIGS. 6 and 7 are side views which show a front end of a direction-controllable drug injection catheter according to another embodiment of the present invention and show respectively a state where the front end has extended in a straight line and a state where the front end has been bent for direction control.

FIG. 6 is a side view showing a direction-controllable drug injection catheter according to another embodiment of the present invention. Referring to FIG. 6, a catheter 200 includes the drug injection part 110, a support 220, and a channel opening and closing means (not shown). Since the drug injection part 110 and the channel opening and closing means (not shown) are the same as those described with reference to FIGS. 2 to 5, the detailed description thereof will be omitted.

Figure 7:
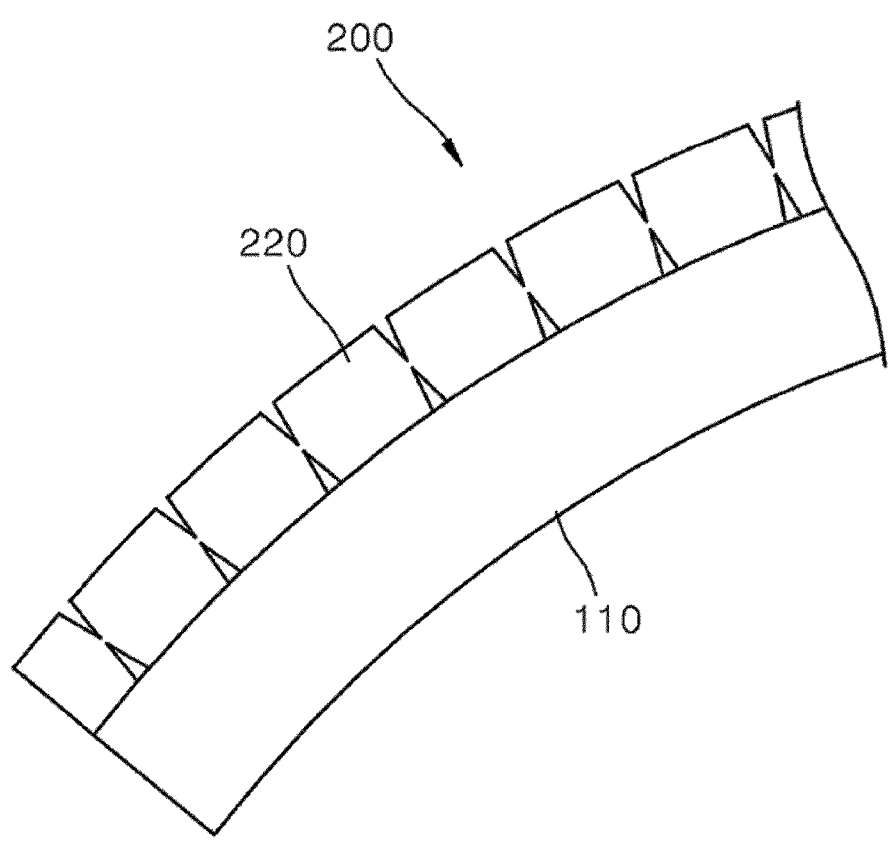

The support 220 includes a base part 221 and a plurality of bonding portions 122 which protrude from the base part 221 and are spaced apart from each other by the gap 123. A plurality of incision portions 223 located corresponding to the gap 123 are formed in the base part 221. The incision portion 223 is formed on the outer surface of the support 120 at the opposite side to the drug injection part 110, so that the catheter can be, as shown in FIG. 7, more easily bent. When the catheter 200 extends, as shown in FIG. 6, in a straight line, incision surfaces of the incision portion 223 become in contact with each other. The structure of the bonding portion 122 and the gap 123 is the same as that described with reference to FIGS. 2 to 5. Therefore, the detailed description thereof will be omitted.

Figure 8:
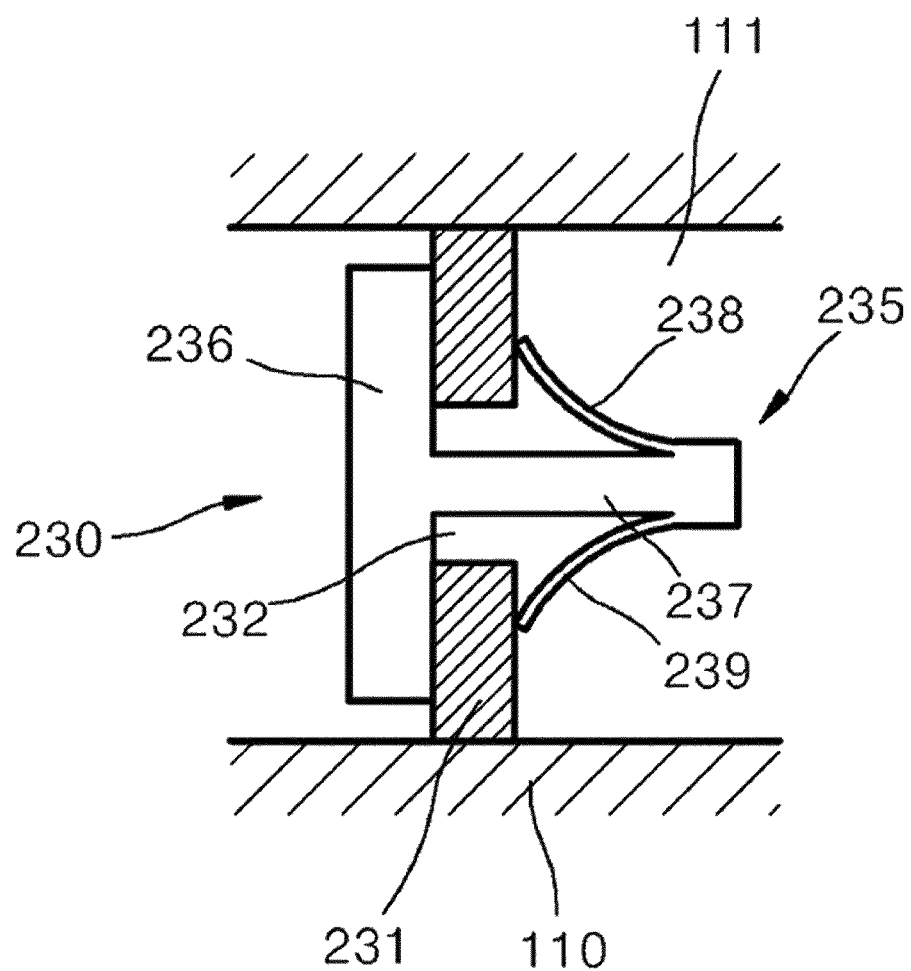
FIGS. 8 and 9 show another embodiment of a channel opening and closing means shown in FIG. 3 and show respectively a closed state and an open state.
Figure 9:
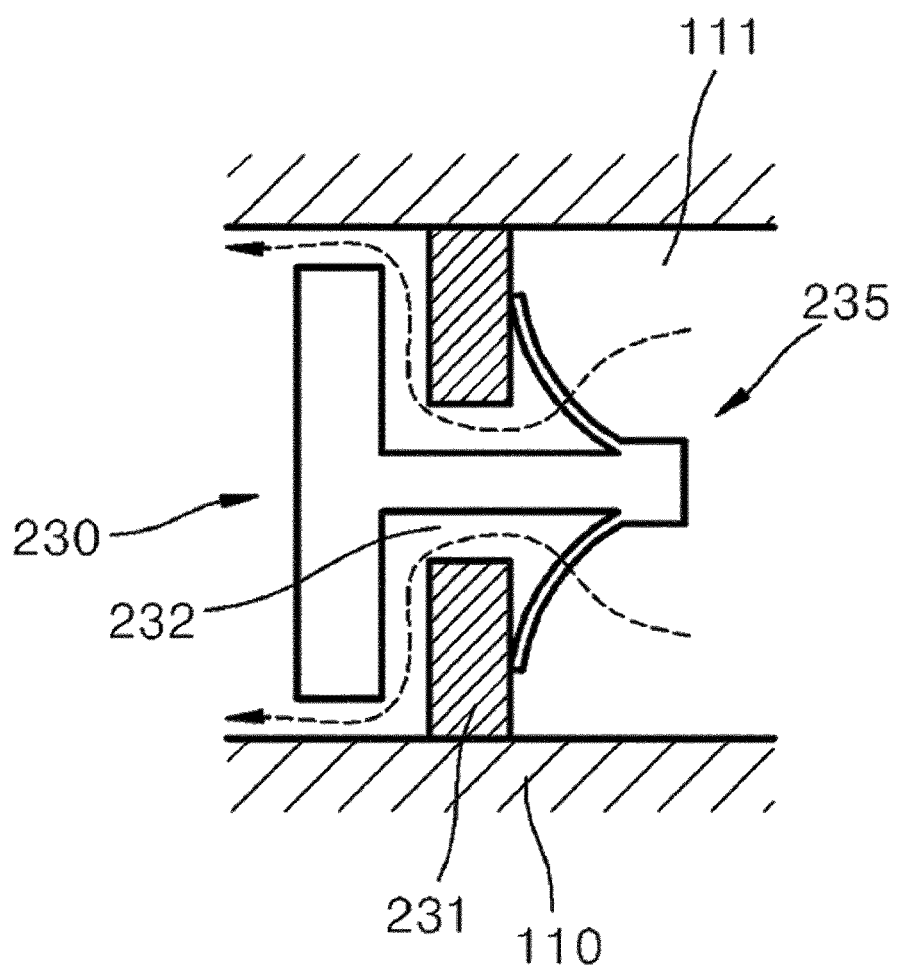

FIG. 8 shows another embodiment of the channel opening and closing means shown in FIG. 3. Referring to FIG. 8, the channel opening and closing means 230 includes a support wall 231 and an opening and closing member 235 coupled to the support wall 231. The support wall 231 is installed on the wall of the drug injection channel 111 formed in the drug injection part 110. A through-hole 232 through which the drug passes is formed in the central portion of the support wall 231. The opening and closing member 235 includes a cover 236, an extension rod 237, and an elastic support 238. The cover 236 has a plate shape and is located downstream with respect to the support wall 231. The cover 236 is larger than the through-hole 232 formed in the support wall 231, thereby opening and closing the through-hole 232. The extension rod 237 has an outer diameter less than that of the through-hole 232 and extends through the through-hole 232. The cover 236 is located on the downstream end of the extension rod 237. The elastic support 238 is located at the upstream of the extension rod 237. The support wall 231 is located between the cover 236 and the elastic support 238, and the elastic support 238 is integrally formed with the extension rod 237 on the opposite side to the cover 236. The elastic support 238 includes a plurality of support wings 239 which radially extend outwardly from the extension rod 237 and of which ends contact the support wall 231. Although not shown in detail, the drug is able to pass between the plurality of the support wings 239. The support wings 239 elastically support the extension rod 237 in a bent state where they are inclined toward the upstream the further it is radially and outwardly from the extension rod 237 and are more opened toward the end thereof contacting the support wall 231. Accordingly, the cover 236 receives a force toward the upstream, and thus, closes stably the through-hole 232. In this state, when a pressure by the drug in the drug injection channel 111 becomes higher than a certain value, the cover 236 is, as shown in FIG. 9, pushed downward, and thus, the through-hole 232 is opened, so that the drug is released as indicated by arrows.

While the present invention has been described by way of the embodiment thereof, the present invention is not limited to this. The embodiment can be modified or changed without departing from the spirit and scope of the present invention, and it can be understood by those skilled in the art that such modification and change belong to the present invention.

The invention claimed is:

1. A catheter extending along a central axis "A", the catheter comprising:
   a drug injection part in which a drug injection channel has been formed;
   a channel opening and closing means which opens and closes the drug injection channel; and
   a steering structure which is rotationally asymmetric with respect to the central axis "A" and varies according to a pressure change of the drug injection channel for the purpose of steering.

2. The catheter of claim 1, wherein the steering structure comprises a support which is bonded to one side outer surface of the drug injection part.

3. The catheter of claim 2, wherein the support comprises a base part, and a plurality of bonding portions which protrude from the base part and have ends bonded to the drug injection part.

4. The catheter of claim 3, wherein the plurality of the bonding portions are disposed in a row along an extension direction of the drug injection channel, and wherein a gap is formed between two adjacent bonding portions among the plurality of the bonding portions.

5. The catheter of claim 3, wherein the bonding portion has a shape which becomes narrower toward the end thereof.

6. The catheter of claim 3, wherein in the base part, a plurality of incision portions are formed on the opposite side to the bonding portion, and wherein the incision portion is located corresponding to the gap.

7. The catheter of claim 2, wherein the support is made of a material having a modulus of elasticity greater than that of the drug injection part.

8. The catheter of claim 2, wherein the drug injection channel is eccentrically located with respect to the whole central axis of the catheter, and wherein the support is located on the opposite side to an eccentric direction of the drug injection channel.

9. The catheter of claim 1, wherein the channel opening and closing means comprises a film-shaped fracture portion which is installed on the drug injection channel and is destroyed by a pressure of the drug.

10. The catheter of claim 1, wherein the channel opening and closing means comprises a support wall which is installed on the drug injection channel and has a through-hole formed therein, and an opening and closing member which opens and closes the through-hole,
   wherein the opening and closing member comprises a cover which is located further downstream than the support wall and opens and closes the through-hole, an elastic support which is located further upstream than the support wall, and an extension rod which passes through the through-hole and connects the cover with the elastic support,
   wherein the elastic support comprises a plurality of support wings which radially extend outwardly from the extension rod and of which ends contact the support wall.

* * * * *